(12) United States Patent
Boulanger

(10) Patent No.: US 6,200,297 B1
(45) Date of Patent: Mar. 13, 2001

(54) SANITARY ABSORBENT ARTICLE WITH SIDE BARRIERS AGAINST LEAKAGE

(75) Inventor: Roger Boulanger, Ste-Julie (CA)

(73) Assignee: Johnson & Johnson Inc., Montreal (CA)

( * ) Notice: Subject to any disclaimer, the term of this patent is extended or adjusted under 35 U.S.C. 154(b) by 501 days.

(21) Appl. No.: 08/676,454

(22) Filed: Jul. 8, 1996

Related U.S. Application Data

(63) Continuation-in-part of application No. 08/635,348, filed on Apr. 19, 1996, now abandoned.

(51) Int. Cl.$^7$ ............................................. A61F 13/15
(52) U.S. Cl. ................. 604/385.04; 604/366; 604/387
(58) Field of Search ............................ 604/365, 366, 604/388.1, 386, 387, 389, 385.04

(56) References Cited

U.S. PATENT DOCUMENTS

| | | | |
|---|---|---|---|
| 4,496,359 | * 1/1985 | Pigneul | 604/387 |
| 5,344,416 | * 9/1994 | Niihara | 604/385.1 |
| 5,387,210 | * 2/1995 | Murakami | 604/396 |
| 5,389,094 | * 2/1995 | Lavash et al. | 601/385.1 |
| 5,490,847 | * 2/1996 | Correa et al. | 604/385.1 |

FOREIGN PATENT DOCUMENTS

| | | | | |
|---|---|---|---|---|
| 2244653 | * 12/1991 | (GB) | | 604/387 |
| 9304651 | * 3/1993 | (WO) | | 604/387 |

* cited by examiner

Primary Examiner—John G. Weiss
Assistant Examiner—K. M. Reichle
(74) Attorney, Agent, or Firm—James P. Barr

(57) ABSTRACT

A sanitary absorbent article is provided which has a generally rectangular main body and two tabs extending from the main body for use in securing the article to the undergarment of the user. A layered structure having a permeable cover, an absorbent system and a barrier layer is provided. The barrier layer is folded around the longitudinal edges of the product and bonded to the cover layer so that liquid collection pockets are formed along the interface between the main body of the product and the tabs when the tabs are pulled into place.

14 Claims, 2 Drawing Sheets

SANITARY ABSORBENT ARTICLE WITH SIDE BARRIERS AGAINST LEAKAGE

This is a Continuation-in-Part Application of commonly assigned application, Ser. No. 08/635,348 filed on Apr. 19, 1996.

FIELD OF THE INVENTION

The present invention relates to a sanitary absorbent product, such as a sanitary napkin, diaper or urinary protection article, which is worn in contact with the skin of the wearer for the purpose of absorption and holding of body liquids and, more particularly, to an absorbent product having tabs extending laterally for attachment to the undergarment of the wearer.

BACKGROUND OF THE INVENTION

The typical design for winged or tabbed sanitary napkins includes a central absorbent body, and two tabs for wrapping around the edges of the undergarment and holding the product in place. A problem with the early designs for sanitary napkins with tabs was that when the tabs were pulled into place, there was no effective barrier to protect against leakage along the side of the napkin. The pulling of the tabs can also result in the central absorbent body surface sloping away from the user in the region adjacent to the tabs, thus making side leakage more likely to occur in this area.

SUMMARY OF THE INVENTION

It is an object of the present invention to provide a sanitary absorbent product with tabs, which is capable to offer enhanced protection against side leakage.

As embodied and broadly described herein, the invention provides a sanitary absorbent product comprising:

a layered elongated main body, comprising from top layer to bottom layer a cover layer which is permeable to liquid, at least one absorbent layer and a barrier layer which is impermeable to liquid, said main body having two opposed longitudinal edges;

two tabs projecting laterally from said longitudinal edges of said main body and adapted to be folded around a crotch portion of an undergarment; and a pocket adjacent to each tab which is capable of collecting body exudate, said pocket including an inlet opening providing a means of entrance to body exudate in said pocket, said pocket being responsive to a lateral outward tension applied to the tab that would occur during attachment of the tab to undergarment of the wearer to cause an increase in size of said inlet opening, thereby enhancing an ability of said pocket to collect body exudate.

In a most preferred embodiment the longitudinal peripheral edge portions of the main body are folded over the cover layer adjacent the longitudinal edges of the main body and thermally bonded to the cover layer along their entire length except in the vicinity of the tabs where the liquid collecting pockets are formed. The tabs are continuous with the folded over portions. When the tabs are subjected to outward tensile force which occurs during the attachment of the tabs to the undergarment of the wearer, the tension is transmitted to the pockets and causes them to open-up.

As embodied and broadly described herein the invention further provides a sanitary napkin, comprising:

a layered elongated main body, comprising from top layer to bottom layer a cover layer which is permeable to liquid, at least one absorbent layer and a barrier layer which is impermeable to liquid, said main body having two opposed longitudinal edges and two opposed lateral edges;

two tabs extending laterally from the longitudinal edges in a direction away from said main body, said tabs being intermediate said lateral edges, each tab comprising a barrier layer element continuous with the barrier layer of said main body, and a cover layer element continuous with the cover layer of said main body; and portions of said barrier layer being folded over the longitudinal edges of the main body and affixed to said main body along said longitudinal edges at four regions proximate intersections of said tabs with said main body, each region excluding at least part of a line of intersection between said main body and a respective tab;

whereby a lateral force which is applied to the tabs during the attachment of said tabs to an undergarment, results in the formation of wells along an interface between the tabs and the main body for collection of liquid having been exuded by the user and which may leak in a lateral direction.

As embodied and broadly described herein, the invention also provides a method of making a sanitary absorbent product, said method comprising the steps of:

cutting an absorbent layer having two opposed longitudinal edges and two opposed lateral edges and having a longitudinal axis;

cutting a liquid permeable flexible sheet material to provide a liquid permeable cover layer and cutting a liquid impermeable flexible sheet material to provide a fluid impermeable barrier layer, wherein the cover layer and the barrier layer have respective main body portions and two tabs extending laterally from the sides of the main body portions;

sandwiching the absorbent layer between the cover layer and the barrier layer;

adhering the cover layer to the barrier layer about their respective outer edge margins to form a flange;

folding the flange around the longitudinal edges of the main body onto the cover layer to form a pair of folded over portions and bonding each folded over portion to the cover layer all along a respective longitudinal edge of said main body with the exception of a line of intersection between the tab and said main body.

BRIEF DESCRIPTION OF THE DRAWINGS

The invention will now be described in greater detail with reference to the accompanying drawings, in which.

DETAILED DESCRIPTION OF THE INVENTION

Figure 1:
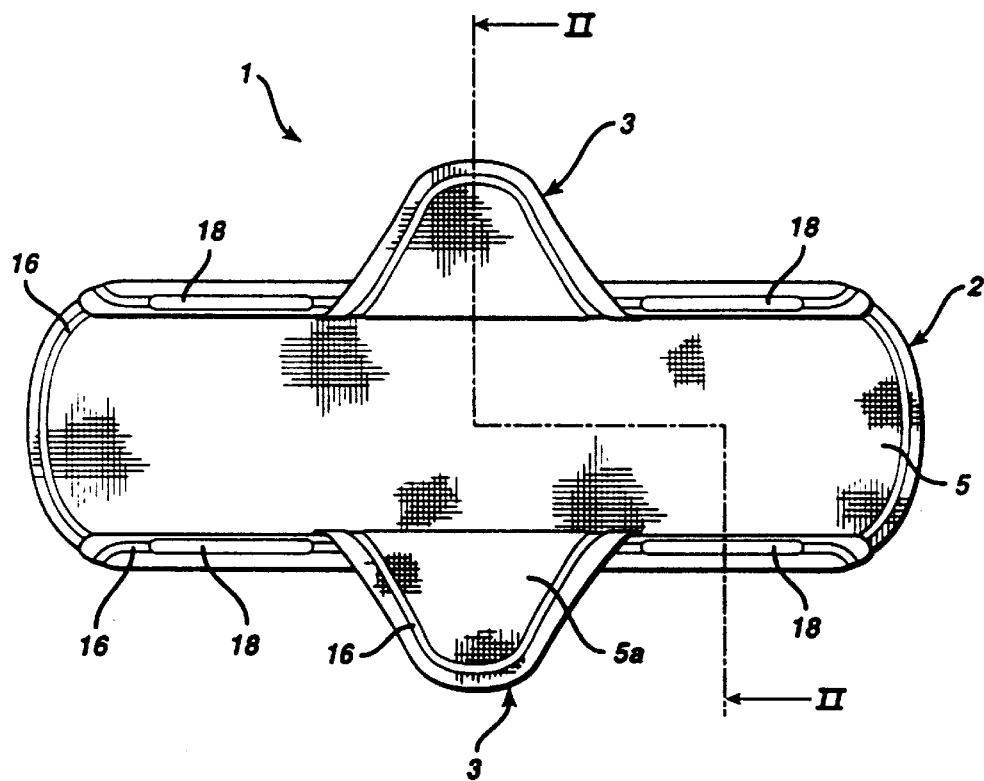
FIG. 1 is a plan view of a sanitary napkin.
Figure 2:
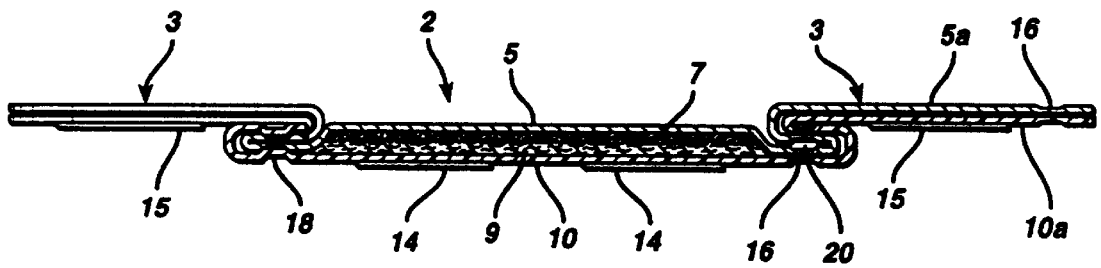
FIG. 2 is a sectional view of the sanitary napkin taken on line II—II of FIG. 1.

Referring firstly to FIGS. 1 and 2, a sanitary napkin 1 comprises an elongated main body 2 with two laterally extending tabs 3. The main body 2 is made in a layered manner and includes from the top down a cover layer 5, an optional transfer layer 7, an absorbent layer 9, and a barrier layer 10. The tabs 3 have a barrier layer 10a which is continuous with the barrier layer 10 of the body 2 and a cover layer 5a which is continuous with the cover layer 5 of the body 2. The barrier layer 10 is provided with two longitudinally extending adhesive bands 14 for adhesion of the main body 2 to the user's undergarment and the barrier layer 10a is provided with adhesive patches 15 on the tabs 3 for securing the tabs to garment facing surface of the undergarment. As is conventional, silicon coated paper (not shown) is provided as a temporary protective cover for the adhesive strips 14 and patches 15.

The cover layer 5 is a liquid permeable, flexible layer of woven or nonwoven fiber and it may have a decorative design. Alternatively, the cover layer 5 may be made of perforated polymeric film.

The optional transfer layer 7, is under the cover layer and may be made of cellulose, bi-component fibers and combinations thereof, is a high void volume porous structure capable of fast liquid acquisition. The ability of the transfer layer to rapidly absorb liquid from the cover layer prevents the body exudate from pooling on the cover layer, thus minimizing the discomfort of the user. This feature also reduces the likelihood of body exudate from leaking past the side edges of the sanitary napkin. The transfer layer 7 is glued to the cover layer 5 above and to the absorbent layer 9 below.

The absorbent layer 9, which may be made of cellulosic pulp fluff, sphagnum moss particles, superabsorbent polymers, synthetic fibers and the like and combinations thereof, provides for the actual absorption of the collected fluid. The transfer layer 7 provides a rapid absorption of liquid from the surface of the napkin where it is retained until the absorbent layer 9, more slowly acquires the liquid from the transfer layer. The liquid is initially absorbed near the place where it has come through the transfer layer 7, but subsequently spreads itself out within the absorbent layer 9.

The barrier layer 10 which may be made of any flexible liquid impermeable material, and is preferably polyethylene, is below the absorbent layer 9 and is impermeable to liquid. Thus, liquid collected by the absorbent layer 9 cannot egress from the absorbent structure to the user's undergarment (not shown).

In manufacturing the napkin 1, the barrier layer 10 and the cover layer 5 are generally cut to substantially the same size, having elongate main body areas which are slightly wider and longer than the transfer layer 7 and the absorbent layer 9, and with two laterally extending tabs 3 as discussed above. The napkin 1 is sealed around the edges, preferably with a continuous thermal bond 16 between the barrier layer 10 and the cover layer 5 to form a flange. This bonding is performed along the outer perimeter of the tabs 3, along the outer peripheral edge of the main body 2, and optionally between the main body and the tabs, to form a continuous closure line around the transfer layer 7 and the absorbent layer 9. The longitudinal peripheral edge portions of the main body are then folded over the cover layer side along the longitudinal edges of the napkin, and bonded to the cover layer 5 with either discrete or continuous elongated thermal bonds 18 which run from points near the end corners of the body 2 to points where the tabs 3 begin as illustrated. No additional bonding is performed in the area of the cover layer 5 adjacent to where the tabs 3 project and thus, the barrier layer 10 and cover layer 5 are folded over, but left unattached in these places.

It will be noted, particularly from FIG. 2 that the transfer layer 7 and the absorbent layer 9 remain well within the region whose boundary is defined by the superposed bond sites 16 and 18. In a variant (not shown in the drawings), the width of the transfer layer 7 and of the absorbent layer 9 may be increased so that the bonds 16 and 18 are no longer superposed to one another. In this arrangement, the continuous bond line 16 extends closer to the edge of the transfer layer/absorbent layer structure and the bond 18 is displaced inwardly and overlaps the transfer layer. In the embodiment depicted in the drawings the longitudinal peripheral portions that are folded over the main body include solely portions of the cover layer 5 and the barrier layer 10. Optionally, the folded over portions may also include portions of the transfer layer 7 or of the absorbent layer 9.

Figure 3:
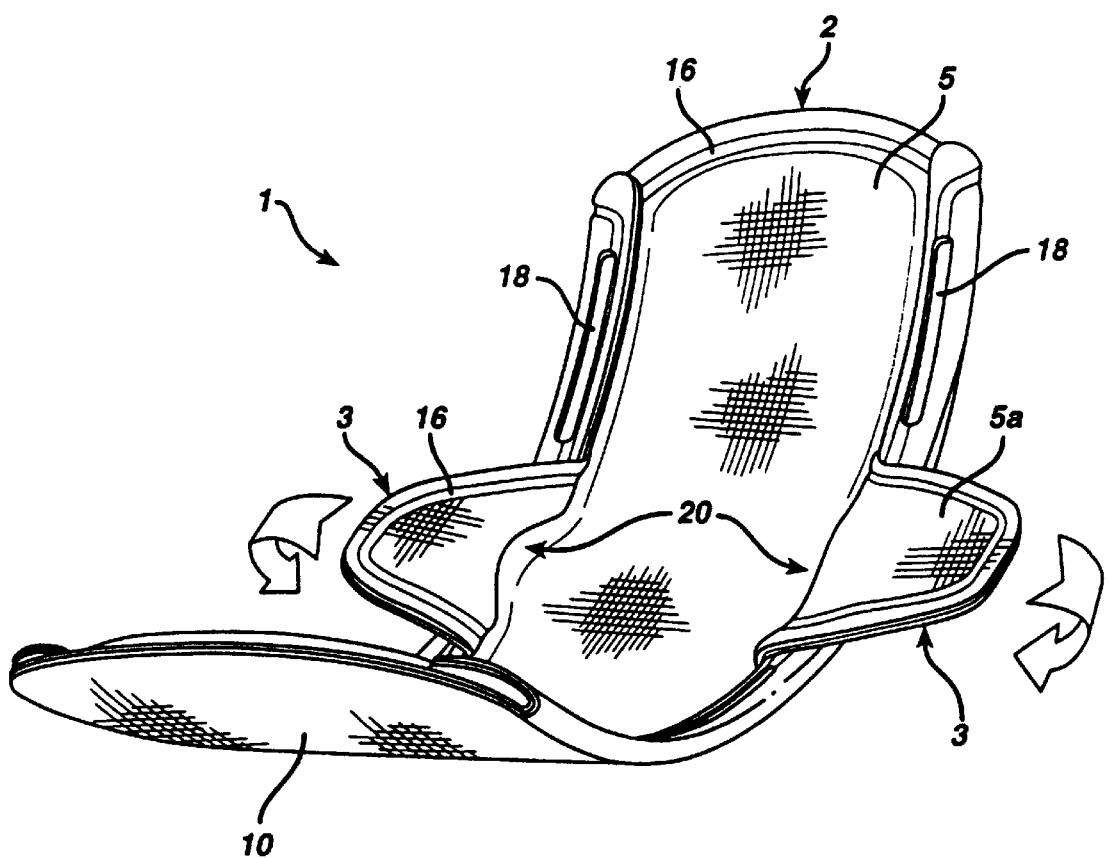
FIG. 3 is a view of the sanitary napkin of FIG. 1 in a curved configuration similar to that which it would attain when applied against the perineal region of the user, also showing the tabs as they would appear just prior to being folded about the edges of the undergarment.

As indicated above, the tabs 3 have adhesive patches 15 so that when the tabs are wrapped around the edges of crotch portion of the undergarment, they may adhere to the outer side of undergarment and thereby provide additional security for the placement of the napkin 1. Due to the fact that no bonding of the barrier layer 10 to the cover layer 2 has been performed in the region adjacent to the tabs 3, fluid collection pockets 20, continuous with the tabs 3 form along the tab/body interfaces. When the tabs are pulled outwardly, as shown in FIG. 3, the pockets 20 open-up, which has the effect of increasing the size of their inlet openings for enhancing the ability of the pockets to intercept body exudate. In traditional designs, when the tabs are pulled into place, the main absorbent body attains a convex surface cross-section near the tabs, sloping away from the user, which tends to cause some flow of liquid toward the edges of the napkin resulting in leakage. The pockets 20 in the current embodiment of the invention tend to prevent the leakage of liquid which has flowed toward the edges near the tabs 3 by providing the capacity to collect and retain the liquid.

The location of the pockets 20 is continuous with the tabs and generally coincides with the transverse centerline of a substantially symmetrical napkin, where body exudate is intended to be deposited. This represents an optimal placement because the risks of side leakage are greater in that area.

The ability of the pockets 20 to provide a liquid arresting function depends to some extent on the width of the pockets which is defined by the distance between the bond sites 18. It will be apparent to those skilled in the art that the width of the pockets 20 may be varied to suit different applications by adjusting the spacing between the bond sites 18.

The manner in which the napkin is used is as follows. First, the silicon coated paper is peeled off from the main body 2 of the napkin 1 to expose the adhesive strips 14. The napkin 1 is then placed in the crotch area of the inner side of the user's undergarment and secured there with the adhesive bands 14. The silicon coated papers are then peeled off from the tabs 3 exposing the adhesive patches 15 on the tabs 3. The tabs 3 are folded around and secured to the outer surface of the crotch area of the undergarment with the adhesive patches 15. The tabs 3 may or may not overlap one another, depending upon their length. During the placement of the tabs 3, the outward lateral tensioning of the tabs 3 opens the pockets. Liquid which is exuded by the user is first collected by the transfer layer 7 which functions to quickly take-up liquid deposited on the cover layer. Then absorption and subsequent storage of most of the liquid by the absorptive layer 9 occurs. However, a rapid fluid discharge may result in some liquid which fails to be absorbed and which has a tendency to flow toward the side of the napkin 1. This usually will occur near the center of the longitudinal axis of the napkin near the tabs because this is where most of the flow originates. Liquid which makes it all the way to the side of the napkin will be collected in the pockets 20 which were formed adjacent to the tabs 3, thereby preventing liquid from leaking past the longitudinal edges of the napkin and subsequently staining the user's undergarment.

In FIG. 3, the orientation of the napkin as it would appear after having been installed with the main adhesive strips, but prior to the complete securement of the tabs 3, is shown. The curvature of the main body 2 follows that of the user's crotch. The tabs 3, having been pulled laterally open-up the pockets 20 along the interface between the tabs and the main body 2.

I claim:

1. A sanitary absorbent product comprising;
    a layered elongated main body, a cover layer which is permeable to liquid, a barrier layer which is impermeable to liquid and at least one absorbent layer between the cover layer and the barrier layer, said main body having two opposed longitudinal edges
    two tabs, each tab projecting laterally from a respective longitudinal edge of said main body and which are adapted to be folded about a crotch portion of a wearer's undergarment; and, wherein said cover layer and said barrier layer are coextensive, and both layers are folded over together along said longitudinal edges of said main body, both layers being bonded to said cover layer along each respective longitudinal edge of said main body with the exception of at least a portion of a line of intersection between each tab and said main body remains unbonded to form a pocket adjacent to each tab which is capable of collecting body exudate that may flow in a lateral direction, said pocket including an inlet opening providing a means of entrance to body exudate in said pocket, said pocket being responsive to a lateral outward tension applied on the tab that would occur during attachment of the tab to the undergarment of the wearer wherein the application of lateral outward pressure causes an increase in size of said inlet opening, thereby enhancing an ability of said pocket to collect body exudate.

2. The sanitary absorbent product as defined in claim 1, wherein each tab is continuous with a respective adjacent pocket.

3. The sanitary absorbent product as defined in claim 1, wherein said layers are bonded along each respective longitudinal edge of said main body by thermal bonds.

4. The sanitary absorbent product as defined in claim 1, wherein said tabs are continuous with said longitudinal edges.

5. The sanitary absorbent product as defined in claim 1, wherein said cover layer and said barrier layer are bonded to said cover layer along each respective longitudinal edge of said main body in a continuous seal line extending from one end of the pocket toward an extremity of the longitudinally extending peripheral portion.

6. The sanitary absorbent product as defined in claim 1, wherein said product is a sanitary napkin.

7. A sanitary napkin, comprising:
    a layered elongated main body, comprising a cover layer which is permeable to liquid, a barrier layer which is impermeable to liquid and at least one absorbent layer between said cover layer and said barrier layer, said main body having two opposed longitudinal edges and two opposed lateral edges;
    two tabs extending laterally from the longitudinal edges of said main body in a direction away from said main body, said tabs being intermediate said lateral edges, each tab comprising a barrier layer element continuous with the barrier layer of said main body, and a cover layer element continuous with the cover layer of said main body and being adapted to be folded over a crotch portion of an undergarment; and
    portions of said barrier layer being folded over the longitudinal edges of the main body and affixed to said main body along each respective longitudinal edge of said main body with the exception of at least a portion of a line of intersection between each tab and said main body remains unbonded;
    wherein a lateral force applied to said tabs during an attachment of said tabs to the undergarment results in the formation of a well along an interface between each of said tabs and the main body for collection of liquid having been exuded by a user.

8. The sanitary napkin according to claim 7, wherein said cover layer and said barrier layer are coextensive, and both layers are folded over together along said longitudinal edges of said main body and affixed to said cover layer.

9. The sanitary napkin according to claim 8, wherein the portions of said barrier layer folded over the longitudinal edges of the main body are thermally bonded to said main body.

10. The sanitary napkin according to claim 7, wherein said cover layer element and said barrier layer element of each tab are bonded to one another along a peripheral portion of the tab.

11. The sanitary napkin according to claim 7, wherein said cover layer and said barrier layer are thermally bonded to one another along a peripheral portion of said main body.

12. The sanitary napkin according to claim 11, wherein said cover layer element and said barrier layer element of each tab are thermally bonded to one another along a peripheral portion of the tab.

13. The sanitary napkin according to claim 7, wherein said barrier layer includes at least one adhesive zone to affix said sanitary napkin to the undergarment of the user.

14. A method of making a sanitary absorbent product, said method comprising the steps of:
    forming an absorbent layer having two opposed longitudinal edges and two opposed lateral edges and having a longitudinal axis;
    cutting a liquid permeable flexible sheet material to form a liquid permeable cover layer;
    cutting a liquid impermeable flexible sheet material to form a liquid impermeable barrier layer, wherein the permeable cover layer and the impermeable barrier layer have respective central main body portions defined by two opposed longitudinal edges and two opposed lateral edges and further comprising two tabs extending laterally from their respective longitudinal edges;
    sandwiching the absorbent layer between the cover layer and the barrier layer;
    adhering the cover layer to the barrier layer around a peripheral edge margin to form a flange;
    folding the flange around the longitudinal edges of the main body to form a pair of folded over portions and bonding each folded over portion to the cover layer all along a respective longitudinal edge of said main body with the exception of at least a portion of a line of intersection between each tab and said main body.

* * * * *